US00PP25577P3

(12) United States Plant Patent
Meinl

(10) Patent No.: US PP25,577 P3
(45) Date of Patent: May 26, 2015

(54) ***HYDRANGEA* PLANT NAMED 'HORWACK'**

(50) Latin Name: *Hydrangea macrophylla*
Varietal Denomination: HORWACK

(71) Applicant: Jungpflanzen Claus & Torsten Kühne GbR, Dresden (DE)

(72) Inventor: Katrin Meinl, Dresden (DE)

(73) Assignee: Jungpflanzen Claus & Torsten Kühne, Dresden (DE)

( * ) Notice: Subject to any disclaimer, the term of this patent is extended or adjusted under 35 U.S.C. 154(b) by 108 days.

(21) Appl. No.: 13/986,489

(22) Filed: May 8, 2013

(65) Prior Publication Data

US 2013/0269074 P1 Oct. 10, 2013

Related U.S. Application Data

(60) Provisional application No. 61/688,640, filed on May 18, 2012.

(51) Int. Cl.
*A01H 5/02* (2006.01)

(52) U.S. Cl.
CPC ..... *A01H 5/02* (2013.01)
USPC ..... Plt./250

(58) Field of Classification Search
CPC ..... A01H 5/02; A01H 5/00; A01H 1/02
USPC ..... Plt./250
See application file for complete search history.

(56) References Cited

PUBLICATIONS

Who-Sells-it. 2011 Ornamentals by Ball Horticultural Dec. 9, 2010, retrieved on Oct. 9, 2014, retrieved from the Internet at <http://www.who-sells-it.com/cy/ball-horticultural-4605/2011-ornamentals-22273/page-24.html> p. 24.*

* cited by examiner

*Primary Examiner* — June Hwu
(74) *Attorney, Agent, or Firm* — Penny J. Aguirre

(57) ABSTRACT

A new cultivar of *Hydrangea macrophylla* named 'HORWACK' that is characterized by its mophead type inflorescences with showy fertile flowers and smaller less numerous non-showy fertile flowers. its showy flowers that are bicolor with bright green and deep pink sepals, its remontant blooming habit, blooming in mid summer and repeat blooming in fall, its remontant blooming habit, its act plant habit with good branching, and its good disease resistance to powdery mildew and botrytis.

1 Drawing Sheet

Genus/species: *Hydrangea macrophylla.*
Varietal denomination: 'HORWACK'.

BACKGROUND OF THE INVENTION

The present invention relates to a new and distinct cultivar of *Hydrangea macrophylla* and will be referred to hereafter by its cultivar name, 'HORWACK'. 'HORWACK' represents a new big leaf *hydrangea*, a perennial shrub grown for landscape use.

'HORWACK' arose from an ongoing breeding program by the Inventor with objectives of developing new cultivars of *Hydrangea* with improved disease resistance, good branching, with induction of primarily sterile flowers.

'HORWACK' originated from a cross conducted in the Inventor's trial garden in April of 2004 in Dresden, Germany between the cultivar 'Green Shadow' as the female parent and an unnamed plant of *Hydrangea macrophylla* from the Inventor's breeding program, designated as clone no. 59-96/1. The new *Hydrangea* was selected as a unique single plant from the progeny of the above cross in April of 2006.

Asexual propagation of the new cultivar was first accomplished by softwood stem cuttings in Dresden, Germany in June of 2006 by the Inventor. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'HORWACK' as a unique cultivar of *Hydrangea macrophylla.*

1. 'HORWACK' exhibits showy flowers that are bicolor with bright green and deep pink sepals.
2. 'HORWACK' exhibits mophead type inflorescences with showy flowers and smaller less numerous non-showy fertile flowers.
3. 'HORWACK' exhibits a remontant blooming habit, blooming in mid summer and repeat blooming in fall.
4. 'HORWACK' exhibits a compact plant habit with good branching.
5. 'HORWACK' exhibits dark green-foliage.
6. 'HORWACK' has shown resistance to powdery mildew and botrytis.

'GREEN SHADOW', the female parent of 'HORWACK', differs from 'HORWACK' in having showy flowers that are bigger, less numerous, and less bright in coloration and in having less resistance to botrytis. The male parent, clone no. 59-96/1, differs from 'HORWACK' in having showy flowers that are dark pink without any green coloration and in having a more vigorous growth habit. 'HORWACK' can also be most closely compared to the cultivars; 'Kolmagics' (not patented) and 'HORGEW' (not patented). Both are similar in having bicolor showy flowers that are pink and green. 'Kolmagics' differs from 'HORWACK' in having inflorescences that are more ball-shaped and in having showy flower sepals that are more rounded in shape. 'HORGEW' differs from 'HORWACK' in having showy flower color that is less brilliant and distinct, in having poorer branching, and in having leaves that are lighter green in color.

BRIEF DESCRIPTION OF THE DRAWING

The accompanying colored photograph illustrates the overall appearance and distinct characteristics of the new *Hydrangea*. The plant in the photograph is about one-year-old in age as grown in a greenhouse in a 1-liter container in Dresden, Germany.

The photograph in FIG. 1 provides a view of 'HORWACK' in bloom.

The colors in the photographs are as close as possible with the digital photography and printing techniques utilized and the color codes in the detailed botanical description accurately describe the new *Hydrangea*.

BOTANICAL DESCRIPTION OF THE PLANT

The following is a detailed description of one year-old plants of 'HORWACK' as grown under greenhouse conditions in one-gallon containers in Abbotsford, B.C., Canada. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Remontant, mid-summer and repeats in fall in temperate climates in the U.S.

*Plant habit.*—Compact and mounded.

*Height and spread.*—Reaches about 30 cm in height and 45 cm in width in a one-liter container.

*Hardiness.*—At least in U.S.D A. Zones 5 to 9.

*Diseases resistance.*—Has shown good resistance to powdery mildew and botrytis.

*Propagation.*—Softwood stem cuttings.

*Growth rate and vigor.*—Moderate.

Stem description:

*Stem shape.*—Round.

*Stem strength.*—Strong.

*Stem color.*—New growth; 144B in color, very sparsely covered with lenticels 1 mm in length and 0.5 mm in width, 1 per 3 sq cm, and 200A in color; mature bark; 164D.

*Stem size.*—Average of 23 cm (to base of inflorescence) in length and average of 7 mm in width.

*Stem surface.*—Glabrous, moderately glossy, mature bark; moderately ridged.

*Branching.*—Basal branching, an average of 8 basal in a one-gallon container, no secondary branches without pinching.

*Internode length.*—Average of 3 cm.

Foliage description:

*Leaf shape.*—Broadly elliptic.

*Leaf arrangement.*—Opposite.

*Leaf division.*—Simple.

*Leaf number.*—Average of 12 (6 pairs) per lateral branch.

*Leaf base.*—Cuneate, sometimes oblique.

*Leaf apex.*—Acuminate.

*Leaf margins.*—Serrated.

*Leaf venation.*—Pinnate, conspicuous, color upper surface 145B to 145C, color lower surface 145C.

*Leaf size.*—Average of 13 cm in length and 8 cm in width when mature.

*Leaf attachment.*—Petiolate.

*Leaf surface.*—Smooth with slight sheen on upper and lower surface.

*Leaf color.*—Young foliage upper surface; blend of 144A and 137C, young foliage lower surface; blend of 144A and 144B, mature foliage upper surface; N137A, mature foliage lower surface; 138B.

*Petioles.*—Average of 1.5 cm in length and 3.5 mm in width, 144B in color, surface is smooth and slightly glossy.

Inflorescence description:

*Inflorescence type.*—Terminal flattened-globular compound corymb of rotate-shaped showy fertile flowers and less numerous smaller non-showy fertile flowers held below showy flowers.

*Lastingness of inflorescence.*—Persistent with color lasting about 4 weeks.

*Inflorescence number.*—One per lateral or sublateral stem.

*Inflorescence size.*—Average of 9 cm in height and 6 cm in diameter.

*Flower number.*—An average of 45 showy flowers per inflorescence and 10 non showy fertile flowers per inflorescence.

*Flower fragrance.*—None.

*Flower aspect.*—Upright and outward.

*Flower size.*—Showy flowers; an average of 3 cm in diameter and 1 cm in depth, non-showy flowers; an average of 5 mm in length and 3.5 mm in width.

*Flower buds.*—Showy flowers; an average of 4 mm in length and 3 mm in width, ovate in shape, 144A in color, non-showy flowers; an average of 2 mm in length and 1 mm in width, ovate in shape, 144C in color.

*Peduncles.*—Primary; an average of 1 cm in length and 4 mm in width, vertical, strong, 144B in color, glabrous surface, secondary on corymb; an average of 7 mm in length and 1.5 mm in width, 161B in color with markings of 59A, glabrous surface.

*Pedicels.*—Showy flowers; an average of 1.7 cm in length and 1 mm in width, held at an average angle of 45° to peduncle, blend of 63B and 63C in color, strong, glabrous surface, non-showy flowers; an average of 2 mm in length and 1 mm in width, held at an average angle of 45° to peduncle, 63C in color, stout, glabrous surface.

*Petals.*—(Both flower types); 4, 4 mm in diameter and 2 mm in width, color 63B on upper surface and 63C on lower surface, broadly acute apex, truncate base, entire margins, glabrous on upper and lower surface.

*Sepals.*—(Showy flowers); Average of 4, rotate in arrangement, glabrous and dull surface (both surfaces), ovate in shape, margin is entire, broadly acute apex, broadly cuneate to rounded base, an average of 1.5 cm in length and 1.5 cm in width, color when opening upper and lower surface; a blend of 144C and 144D, color when fully open upper surface; a blend of 144B to 144C with markings of 63C and 59B to 59D, color when fully open lower surface; 144B to 144C with markings of 59B to 59C radiating from base and a thin margin of 59A, color when fully mature upper surface; a blend of 59A to 59C with blotchy markings of 144A near apex, color when fully mature lower surface; a blend of 63B to 63D blended with areas of 143D (most towards apex), non showy flowers; campanulate in shape, fused with 4-starred apex, calyx is 3 mm in length and 2 mm in width, 145C in color with apex margins 145B (inner and outer surfaces), glabrous surface.

Reproductive organs: (Showy and non-showy flowers)

*Stamens.*—Average of 8, anther is oblong in shape, 1 mm in length and 157C in color, filament is 4 mm in length and 63C in color, pollen is moderate in quantity and 144D in color.

*Pistils.*—3, club-shaped, average of 2 mm in length and 1 mm in width, stigma is 0.5 mm in height, rounded and 157C in color, style is an average of 1.5 mm in length and 63C in color, ovary is 145B in color.

*Fruit and seed.*—Has not been observed under the conditions tested to date.

It is claimed:

1. A new and distinct cultivar of *Hydrangea* plant named 'HORWACK' substantially as herein illustrated and described.

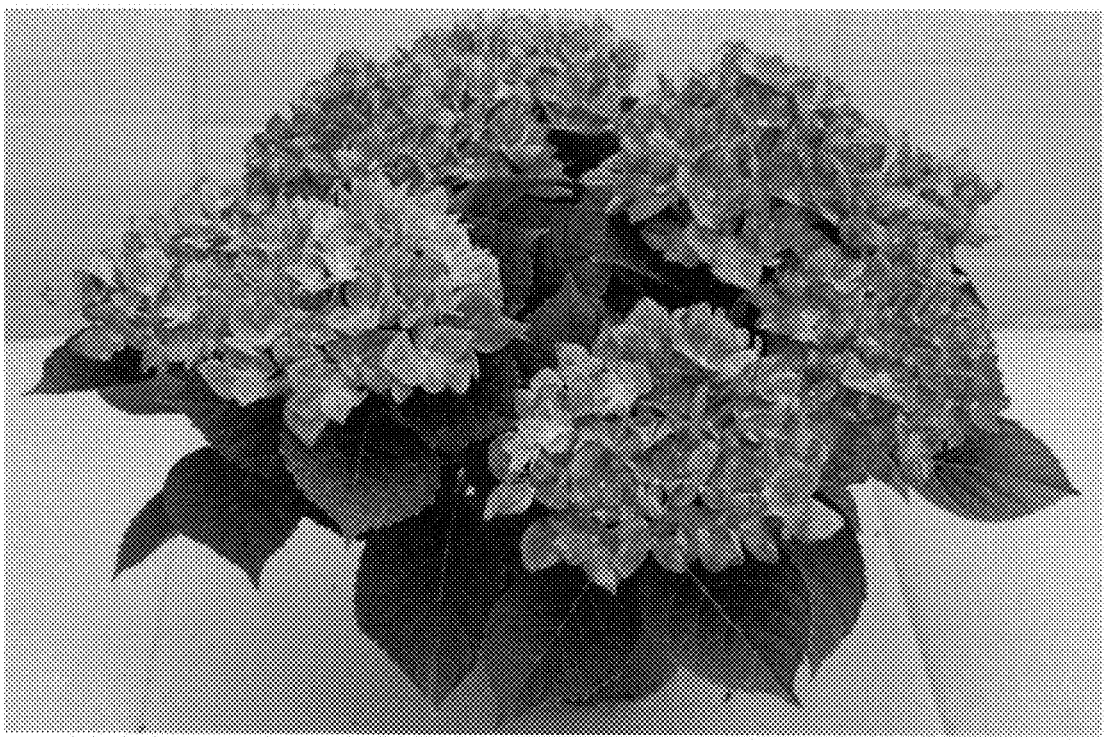

* * * * *